United States Patent [19]
Shorr

[11] Patent Number: 5,415,803
[45] Date of Patent: May 16, 1995

[54] CONCENTRATED BROMINE SOLUTIONS

[75] Inventor: Leonard Shorr, Haifa, Israel

[73] Assignee: Bromine Compounds, Inc., Beer-Sheva, Israel

[21] Appl. No.: 54,190

[22] Filed: Apr. 28, 1993

[30] Foreign Application Priority Data

Apr. 30, 1992 [IL] Israel ................................ 101750

[51] Int. Cl.$^6$ .............. A62D 3/00; C09K 3/00
[52] U.S. Cl. .................. 252/186.44; 423/500; 423/265; 252/187.2; 252/182.34
[58] Field of Search ............ 252/182.12, 182.34, 252/183.13, 183.14, 186.44, 187.2; 423/500, 265

[56] References Cited

U.S. PATENT DOCUMENTS

| | | | |
|---|---|---|---|
| 2,250,379 | 7/1941 | Johnson | 252/183.13 |
| 3,493,654 | 2/1970 | Goodenough et al. | 424/127 |
| 3,558,503 | 1/1971 | Goodenough et al. | 252/187 |
| 4,731,233 | 3/1988 | Thompson et al. | 423/242.7 |
| 4,752,364 | 6/1988 | Dhooge | 204/131 |

FOREIGN PATENT DOCUMENTS

| | | | |
|---|---|---|---|
| 2630088 | 1/1978 | Germany. | |
| 2045218 | 10/1980 | United Kingdom | 423/243.01 |

*Primary Examiner*—Wayne Langel
*Assistant Examiner*—Stuart L. Hendrickson
*Attorney, Agent, or Firm*—Michael N. Meller

[57] ABSTRACT

A novel composition of matter comprises a stable solution of elemental bromine and urea in water.

2 Claims, 1 Drawing Sheet

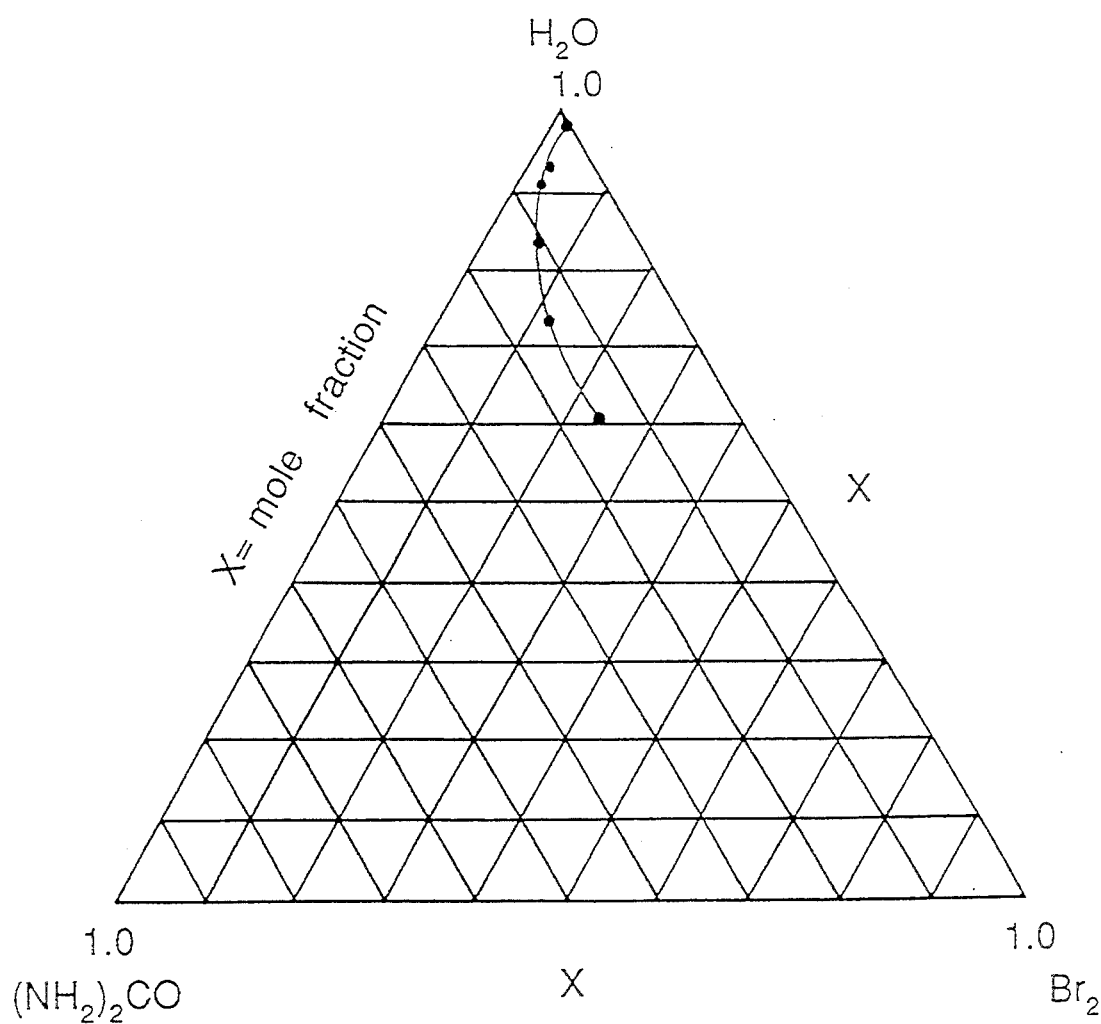

CONCENTRATED BROMINE SOLUTIONS

FIELD OF THE INVENTION

This invention relates to compositions of matter consisting of or comprising stable, concentrated bromine solutions in water and to methods for the transportation of elemental bromine, for effecting bromination reactions and for carrying out treatments in which bromine is the active agent, such as bleaching, disinfection and etching.

BACKGROUND OF THE INVENTION

Elemental bromine is used in the manufacture of a variety of bromine compounds of commercial interest. It is also used, either directly or indirectly, in the desizing of cotton, for bleaching pulp and paper, in hair waving compositions, as a biocide (e.g. water disinfection) in air conditioning absorption fluids and as an etchant. A number of these applications require the use of aqueous solutions containing bromine. However, such use is limited due to the relatively low solubility of bromine in water, which is not influenced significantly by temperature (Kirk-Othmer, Encyclopedia of Chemical Technology, Vol 4, p. 229):

TABLE 1

| TEMP. °C. | SOLUBILITY, g/100 g SOLN |
| --- | --- |
| 5 | 3.54 |
| 10 | 3.60 |
| 20 | 3.41 |
| 25 | 3.35 |
| 40 | 3.33 |
| 53.6 (bp) | 3.50 |

It is unwieldy to transport such dilute solutions and the formation of bromine solutions in water on site presents a variety of technological problems. Thus for example, not only is the solubility of bromine in water low, its rate of dissolution is also low. Bromine is also both volatile and corrosive. Furthermore, at low temperatures, metastable aqueous solutions of bromine in water may be formed. It is therefore of interest to provide a means by which bromine itself or a bromine concentrate can be made available and transported in a readily diluted form for use in these various applications.

To overcome the aforesaid difficulties, it has been suggested to increase the solubility in water by the addition of salts or mineral acids. The following are some examples, at 25° C. (Kirk-Othmer, Vol 4, p. 229):

TABLE 2

| SOLUTE | SOLUTE, g/l SOLN | BROMINE, g/l SOLN |
| --- | --- | --- |
| none | | 34.0 |
| KBr | 119.0 | 216.0 |
| NaBr | 320.0 | 546.0 |
| NaCl | 58.5 | 55.9 |
| Na2SO4 | 63.6 | 23.9 |
| HBr (20.8° C.) | 33.7 | 108.8 |
| HCl (20.8° C.) | 39.0 | 79.2 |

The bromides are seen to be particularly effective due to the formation of complexes in these systems.

However, increasing the solubility of bromine in water in this manner suffers from the nature of the solubilizers themselves. Thus, for example, high salt or acid concentrations cannot be tolerated by many systems. In addition, an ecological waste problem is presented by the need to dispose of the brine or acid solutions which remain after the bromine, originally contained therein, has been used. In some applications involving emulsified systems, such as paint latexes, high salt concentrations can break the emulsions.

Because of these problems, the use of bromine dissolved in other solvents is common, though these are more costly per se, introduce additional costs in solvent recovery, purification and recycling operations, and may even be dangerous. Thus for example, solutions of bromine in methanol are widely used in the etching of semi-conductor materials, in spite of the fact that there is a potential hazard in preparing such solutions [P.T. Bowman, et al, J. Electrochem. Soc. 137 (4), 1309 (1990)].

It is a purpose of this invention to provide aqueous solutions of bromine that are free from objectionable salt or acid components.

It is another purpose of the invention to achieve rapid dissolution of bromine in water.

It is a further purpose to achieve the aforesaid purposes by means which are inexpensive, compatible with a wide variety of applications, safe and ecologically friendly.

It is a further purpose to provide means for the safe and economical transportation of elemental bromine, which means further permit easy recovery and use of the bromine in situ.

It is a still further purpose to provide a convenient and inexpensive solution that is adapted for use as bromination means.

It is a still further purpose to provide a convenient and inexpensive solution that is adapted for use as bleaching, disinfection and etching means and the like.

Other purposes and advantages of the invention will appear as the description proceeds.

BRIEF DESCRIPTION OF THE DRAWING

The drawing illustrates the phase diagram of the bromine-urea-water system.

SUMMARY OF THE INVENTION

The invention is a new composition of matter, which consists of or comprises a stable solution of elemental bromine and urea in water.

Such solutions comprise at least 3.2% by weight of bromine. Solutions comprising at least 5% by weight of bromine are preferred.

Preferably, too, such solutions should contain at least 4% by weight of urea.

The invention further comprises a method of transporting elemental bromine, comprising preparing a solution of bromine and urea in water at a starting point and recovering the bromine from the solution at a final point, a possible means of effecting said recovery being stripping the bromine from the solution by means of a stream of air.

The invention further comprises a method of effecting bromination reactions comprising preparing a solution of urea in water, and dissolving therein the substrate compound to be brominated and the bromine required to effect the bromination, the order of the addition of the substrate compound and the bromine being optional.

The invention further comprises a method of effecting treatments in which bromine is the active agent, comprising preparing a solution of bromine and urea in water and using the solution as the agent for carrying out the treatment.

DETAILED DESCRIPTION OF THE PREFERRED EMBODIMENTS

It has been found that bromine dissolves rapidly and safely in aqueous solutions of urea. For example, the solubility of bromine in an aqueous solution containing 50% urea is approximately an order of magnitude greater than the solubility of bromine in water itself. Furthermore, urea is relatively inexpensive and being a natural product itself, does not present significant ecological problems. On the contrary, in some applications in the agriculture industry, urea can provide added nourishment for the crops. Stable aqueous solutions of urea in water containing more than 3.2% Br have not been known previously and therefore constitute a new composition of matter.

EXAMPLE 1

Bromine was added with stirring to 100 g of a 5% urea solution in water at 20° C., until saturation was reached. A total of 8.1% $Br_2$ was thus added. The resulting solution contained:

7.5% $Br_2$
4.6% urea
87.9% $H_2O$

The density of the solution was 1.05 g/ml.

The following limiting solubility data were collected by gravimetric determinations of the components in separatory funnels which were vigorously shaken to achieve equilibrium.

TABLE 3

| | SOLUBILITY OF BROMINE IN AQUEOUS UREA SOLUTIONS | | | | |
|---|---|---|---|---|---|
| T (°C.) | % Urea in water (Soln. A) | G. $Br_2$ added per 100 g. of Soln. A | % $Br_2$ in Final Soln | pH | Density g/ml |
| 15; 25 | 0 | 3.4 | 3.3 | — | — |
| 20; 30 | 15 | 17.4 | 14.8 | 1.5 | 1.16 |
| 20 | 20 | 23.9 | 16.1 | — | — |
| 20 | 30 | 41.3 | 29.2 | — | — |
| 20 | 40 | 83.5 | 45.5 | — | — |
| 20 | 50 | 151.5 | 60.2 | <1.5 | 1.88 |

The attached drawing illustrates the phase diagram of the bromine-urea-water system.

The method of transporting elemental bromine, according to the invention, will now be exemplified.

EXAMPLE 2

68 Grams of $Br_2$ were added to a solution of 30 g. urea in 30 g. distilled water, in which the bromine dissolved rapidly with only mild mixing. The solution container was stoppered and set aside for 11 days. A slow stream of air was then led into the head space above the solution, by which means all of the bromine contained in the solution was completely removed, leaving a colorless and odorless solution of urea in water.

The method of carrying out treatments in which bromine is the active agent, will now be described with reference to the bleaching of a cellulosic material, specifically paper.

EXAMPLE 3

Bromine was added to ca 10 ml of water in a test-tube. Not all of the bromine dissolved, even with vigorous shaking. A strip of yellow, blue-lined paper (ex Hadera Paper Mills, "60 grams/m², wood-free Direct yellow C.I.-132 paper") was dipped into the upper aqueous phase for just a few seconds. The paper was removed and shaken to remove adhering droplets. After a few minutes, the blue lines faded in those sections of the paper which had been wetted, but the yellow coloration remained.

Urea (ca 1 g.) was added to the aqueous solution, whereby the undissolved bromine remaining on the bottom of the T-tube rapidly dissolved. The concentration of this solution (with respect to bromine) is therefore higher than that of the urea-free solution.

A second strip of the same paper was dipped into the bromine/urea/water solution thus formed, removed after a few seconds and shaken to remove adhering droplets, in the same way. Again the blue lines faded after several minutes, but the yellow color did so as well.

Another example of a method of treatment in which bromine is the active agent, specifically a biocidal or disinfectant treatment, will now be given.

EXAMPLE 4

Liquid bromine was added to a 50% urea solution (50 g urea dissolved in 50 ml $H_2O$) to yield a ca 30% solution of bromine. This solution was diluted 10-fold, titrated (active bromine was found by iodometric titration to be 3.20%, followed by tenfold serial dilutions to provide the bromine concentrations indicated in the following table when introduced into 20 ml of a bacterial suspension contained in Erlenmeyer flasks.

After set time intervals, 0.5 ml aliquots of the treated suspensions were added to 4.5 ml of aqueous thiosulfate solutions to neutralize the bromine. Aliquots were withdrawn from the thiosulfate tubes and diluted (by tenfold serial dilutions) in sterile phosphate buffer. From each dilution 10 microliter samples were withdrawn and applied on Nutrient Agar plates (NA). The spots were allowed to dry and the plates were incubated at 35° C. for 24 hours. The number of surviving bacteria was calculated by multiplying the number of colonies which developed by the dilution factor and dividing by the volume of the deposited spot.

TABLE 4

| $Br_2$ mg/l (ppm) | 320 | 32 | 3.2 | 0.32 | Blank, | Urea 5000 |
|---|---|---|---|---|---|---|
| Time pH (min) | 7 | 7 | 7 | 7 | 7.0 | 8.6 |
| 0 | $4.7 \times 10^7$ | $7.8 \times 10^7$ | $5.8 \times 10^7$ | $3.2 \times 10^7$ | $7.5 \times 10^7$ | $8.0 \times 10^7$ |
| 0.1 | 0 | $8.5 \times 10^7$ | $3.8 \times 10^7$ | $2.4 \times 10^7$ | $5.8 \times 10^7$ | $7.9 \times 10^7$ |
| 1.0 | 0 | 0 | $2.2 \times 10^6$ | $1.3 \times 10^7$ | $8.2 \times 10^7$ | $7.8 \times 10^7$ |
| 5.0 | 0 | 0 | 0 | $8.4 \times 10^6$ | $7.1 \times 10^7$ | $6.7 \times 10^7$ |
| 10.0 | 0 | 0 | | $7.3 \times 10^6$ | $9.2 \times 10^7$ | $5.5 \times 10^7$ |

The results indicate clearly that bromine dissolved in urea solution is active as bromine; at 3.2 ppm, full control was achieved. As expected, urea has no effect on the bacterial viability even at a concentration of 0.5% (=5000 ppm), the highest urea concentration used.

The method of effecting bromination according to the invention will now be exemplified.

EXAMPLE 5

To a solution of 25 g water and 25 g urea at 30° C., 14.0 g of phenol (0.15 mol) was added with stirring. All the phenol dissolved and the mixture was cooled to 25° C. when turbidity started to form. Bromine (15 g, 0.09 mol) was then added dropwise with stirring, maintaining the temperature at 22°–23° C. After the addition, stirring was continued for an additional 0.5 h. Methylene chloride (30 ml) was then added. The organic layer was separated, washed in water (2×30 ml) and dried over $MgSO_4$. Evaporation of the solvent left an oily residue. The product composition was determined by gas chromatography to be as follows (phenol free basis):

| | |
|---|---|
| o-Bromophenol | 12.5% |
| 2,6-Dibromophenol | 2.3% |
| 2,4-Dibromophenol | 24.6% |
| p-Bromophenol | 34.2% |
| Tribromophenol | 26.5% |

The following example demonstrates the use of an aqueous urea solution containing bromine for the purpose of etching gold.

EXAMPLE 6

A 1.2 cm×12.7 cm×0.3 cm specimen bar of polypropylene 50112 (ex Amoco) was cleaned with acetone and gold plated (ca. 300 Å thick layer) by vapor deposition.

The above gold plated bar was dipped into the following solution:

22.5 g $H_2O$
22.5 g Urea (analar grade, ex Merck)
5.0 g Bromine.

Within a few seconds the gold was completely removed from that section of the bar which was immersed in this solution.

While a number of embodiments of the invention have been described by way of non-limitative exemplification, it will be apparent that the same can be carried into practice with many modifications, variations and adaptations within the skill of persons skilled in the art, without departing from its spirit or exceeding the scope of the claims.

I claim:

1. A stabilized composition of matter which comprises a solution of elemental bromine and urea in water, wherein bromine is present in an amount of at least 3.2% by weight and urea is present in an amount of at least 4% by weight wherein the composition is substantially free of salts and acids.

2. A composition of matter according to claim 1, wherein bromine is present in an amount of at least 5% by weight.

* * * * *